United States Patent [19]

Salzman et al.

[11] Patent Number: 4,884,886
[45] Date of Patent: Dec. 5, 1989

[54] BIOLOGICAL PARTICLE IDENTIFICATION APPARATUS

[75] Inventors: Gary C. Salzman; Charles T. Gregg; W. Kevin Grace; Richard D. Hiebert, all of Los Alamos, N. Mex.

[73] Assignee: The United States of America as represented by the Department of Energy, Washington, D.C.

[21] Appl. No.: 302,036

[22] Filed: Jan. 26, 1989

Related U.S. Application Data

[63] Continuation of Ser. No. 180,686, Apr. 8, 1988, abandoned, which is a continuation of Ser. No. 893,074, Aug. 1, 1986, abandoned, which is a continuation-in-part of Ser. No. 699,890, Feb. 8, 1985, abandoned.

[51] Int. Cl.$^4$ .............................................. G01J 4/00
[52] U.S. Cl. ..................................... 356/367; 250/225
[58] Field of Search ....................... 250/225, 574, 576; 356/364–368

[56] References Cited

U.S. PATENT DOCUMENTS

| | | | |
|---|---|---|---|
| 3,612,688 | 10/1971 | Liskowitz | 356/365 |
| 3,785,735 | 1/1974 | Friedman et al. | 356/342 |
| 3,817,634 | 6/1974 | Barron | 356/365 |
| 4,140,902 | 2/1979 | Young | 356/339 |
| 4,306,809 | 12/1981 | Azzam | 356/368 |

OTHER PUBLICATIONS

Salzman, Gary, "Light Scattering Analysis of Single Cells", Cell Analysis, vol. 1, Plenum Pub. Co., 1982, pp. 111–143.
Bickel et al, "Polarized Light Scattering from Biological Systems: A Technique for Cell Differentiation", J. Biol. Physics, vol. 9, 1981, pp. 53–66.
Bickel et al, "Application of Polarization Effects in Light Scattering: A New Biological Tool", Proc. Nat. Acad. Sci., vol. 73, No. 2, pp. 486–490, Feb. 1976.
Salzman et al., "Rapid Indentification of Microorganisms by Circular-Intensity Differential Scattering", App. and Eviron. Microbiology, Nov. 1982, pp. 1081–1085.
Azzam, "Photopolarimetric Measurement of the Mueller Matrix by Fourier Analysis of Single Detected Signal", Optical Letters, vol. 2, No. 6, Jun. 1978, pp. 148–150.
Hunt et al., "A New Polarization-Modulated Light Scattering Instrument", Rev. Sci. Instrum., vol. 44, No. 12, Dec. 1973, pp. 1753–1762.
Azzam, "Simulation of Mechanical Rotation by Optical Rotation", J. Opt. Soc. Am., vol. 68, No. 4, 1978, pp. 518–520.
Thompson et al., "Measurement of Polarized Light Interactions via the Mueller Matrix", Applied Optics, vol. 19, No. 8, pp. 1323–1332.

*Primary Examiner*—Edward P. Westin
*Attorney, Agent, or Firm*—Samuel M. Freund; Ray G. Wilson; Judson R. Hightower

[57] ABSTRACT

An apparatus and method for making multiparameter light scattering measurements from suspensions of biological particles is described. Fourteen of the sixteen Mueller matrix elements describing the particles under investigation can be substantially individually determined as a function of scattering angle and probing radiations wavelength, eight elements simultaneously for each of two apparatus configurations using an apparatus which inclues, in its simplest form, two polarization modulators each operating at a chosen frequency, one polarizer, a source of monochromatic electromagnetic radiation, a detector sensitive to the wavelength of radiation employed, eight phase-sensitive detectors, and appropriate electronics. A database of known biological particle suspensions can be assembled, and unknown samples can be quickly identified once measurements are performed on it according to the teachings of the subject invention, and a comparison is made with the database.

16 Claims, 7 Drawing Sheets $$\begin{pmatrix} F_{11}(\ 0) & F_{12}(\ -\ ) & F_{13}(100) & F_{14}(\ 50) \\ F_{21}(\ -\ ) & F_{22}(\ -\ ) & F_{23}(\ -\ ) & F_{24}(\ -\ ) \\ F_{31}(94) & F_{32}(\ -\ ) & F_{33}(\ 6) & F_{34}(\ 44) \\ F_{41}(\ 4) & F_{42}(\ -\ ) & F_{43}(53) & F_{44}(\ 97) \end{pmatrix}$$

FIG. 3

BIOLOGICAL PARTICLE IDENTIFICATION APPARATUS

BACKGROUND OF THE INVENTION

The present invention relates generally to particle sorting and identification and more particularly to the use of light scattering to identify biological particles in static suspensions. This invention is the result of a contract with the Department of Energy (Contract No. W-7405-ENG-36).

This is a continuation of application Ser. No. 180,686 filed Apr. 8, 1988, now abandoned, which is a continuation of application Ser. No. 893,074 filed Aug. 1, 1986, now abandoned, which patent application is a continuation-in-part of patent application Ser. No. 699,890. "Virus Identification Apparatus," by Gary C. Salzman et al., filed on Feb. 8, 1985, now abandoned.

The rapid identification of viruses and bacteria is of obvious importance in industry, research, and clinical medicine and has been greatly enhanced in recent years. The development of chemiluminescent and enzyme-linked immunoabsorbent assays for the rapid identification of viruses has reduced identification time to 2-4 hours in the most favorable cases. However, identification of microorganisms requires that the cells be isolated and grown in reasonably pure cultures, a process which can taken from 16 hours, again in favorable cases, to several weeks. Thus, despite advances in the availability of automated particle identification systems, virus and bacteria identification still generally require on the order of 24 hours since pure cultures must be grown for the current procedures to be used.

Bacteria and viruses contain biological macromolecules that are asymmetric structures that interact differently with left and right circularly polarized light. Circular intensity differential scattering, which is the differential scattering of left and right circularly polarized light, probes the higher order structure (structure other than the shape of the scattering species) of macromolecular aggregates, and is sensitive to the orientation of such structures relative to the direction of polarization of the incident electromagnetic radiation. The circular intensity differential scattering signal is the amount of light scattered when the incident beam is left circularly polarized minus that scattered when the incident beam is right circularly polarized, divided by the total amount of light scattered by the microorganism. Since the circularly polarized light differentially scattered from an asymmetric structure into a detector is sensitive to the orientation of the structure with respect to the direction of polarization of the incident light beam, and would be different for different orientations of a single particle, it is desirable to measure the circular intensity differentially scattered signal as well as any other polarization sensitive signals from suspensions of the particles of interest. Particles in a suspension are randomly oriented so that the scattering signals derived therefrom represent a spatial average for all of the particles in the path of the light beam. It is fortuitous that clinical virus specimens generally contain a single virus type in most of the cases studied. Moreover, it is straightforward microbiological technology to prepare single strain bacterial specimens and bacterial suspensions therefrom.

The circular intensity differential scattering signal can be related to one element of a 4×4 matrix called the Mueller matrix which describes the scattering of light from an object at a particular angle and wavelength. All of the information in a beam of electromagnetic radiation is contained in a four element vector called the Stokes vector (I, Q, U, V). I is the intensity of the light in a beam of radiation and is customarily normalized to unity. Q, U and V describe the polarization properties of the light beam. Q is the tendency toward horizontal linear polarization. Its value is $+1$ for horizontal linearly polarized light and $-1$ for vertical linearly polarized light. U is the tendency toward linearly polarized light tilted at $+45°$ to the horizontal scattering plane. It has values ranging from $+1$ ($+45°$) to $-1$ ($-45°$). V is the tendency toward right circular polarization. For a right circularly polarized beam, $V=+1$ and for a left circularly polarized beam, $V=-1$. For the apparatus of the present invention, the Stokes vectors of the incident and scattered light are manipulated by a series of optical elements, each represented by a 4×4 Mueller matrix, in order that the intensity component of this vector, $I_f$, for the scattered radiation is made to develop information about the scattering sample which can be extracted by appropriate signal processing. There are ten independent matrix elements which can be determined from the scattering experiments which characterize the scattering particle. Moreover, by utilizing scattering angle and radiation wavelength dependence of the ten parameters, it should be possible to uniquely characterize particles for rapid and positive identification. It is to be stressed that the present invention permits independent determination of ten parameters for a particular wavelength and scattering angle. In all but one of the references to be evaluated hereinbelow, linear combinations of Mueller matrix elements are obtained. Except for the most fortuitous situations, the number of independent pieces of information which can be derived from such linear combinations is far smaller than the number available, thereby reducing the information available to uniquely characterize the particles of interest.

In "Suspended Organic Particles Monitor Using Circularly Polarized Light," invented by John W. Liskowitz, U.S. Pat. No. 3,612,688, issued on Oct. 12, 1971, the inventor describes the use of circular dichroic absorption to detect organic particles suspended in a fluid. Right circularly polarized light and left circularly polarized light are alternatively passed through the sample and the intensity of the transmitted intensity of the circularly polarized components (at 0° scattering angle) is analyzed. The circular dichroic absorption of the sample is represented by the ratio of the component intensities of the absorbed radiation when starting with right circularly polarized light to that when starting with left circularly polarized light. Although the resulting intensity ratio can be related to components of the Mueller matrix describing the scattering process, the use of circularly polarized light in the manner described by the inventor does not permit evaluation of individual components thereof which as mentioned hereinabove, in general does not permit the extraction of the individual components but rather linear combinations thereof with the consequent loss of important information in all but the most fortuitous circumstances. Moreover, the linear combinations contain contributions from terms in the Mueller matrix which have nonzero values for optically inactive particles, such terms having their origin in the size and shape of the particle itself and not in the genetic composition of the particle. The use of quarter-wave retarders generates circularly polarized radiation which leads to the undesirable linear combinations of Mueller matrix elements.

In "Testing of Optically Active Substances by Polarized Radiation," invented by Laurence David Barron and Amy and David Buckingham, U.S. Pat. No. 3,817,634, issued on Jun. 18, 1974, the inventors disclose the use of alternating right and left circularly polarized radiation to irradiate a sample from which a scattered signal is derived which reflects the nature of the optically active substance contained therein in a similar manner to the invention of Liskowitz, supra. The Barron et al. invention contains the same limitations found in Liskowitz, except that Barron et al. restrict the angle of observation to be orthogonal to the incident radiation beam and are investigating scattered radiation, not absorbed radiation. No such restriction is required according to the practice of the subject invention. In fact, much additional information can be derived from the angular dependence of the Mueller matrix elements. Barron et al. also disclose the detection of a Raman signal which is produced by the inelastic scattering of the incident radiation, as opposed to the elastic scattering process of the subject invention. Raman signals tend to be quite weak in the absence of resonance phenomena, and occur at a different wavelength from that of the incident electromagnetic radiation.

Three references by R. M. A. Azzam, "Simulation of Mechanical Rotation by Optical Rotation: Application to the Design of a New Fourier Photopolarimeter," J. Opt. Soc. Am. 68, 518 (1978), "Photopolarimetric Measurement of the Mueller Matrix by Fourier Analysis of a Single Detected Signal," Optics Lett. 2, 148 (1978), and "Polarimeter," U.S. Pat. No. 4,306,809, issued on Dec. 22, 1981, describe a procedure involving Fourier analysis of the detected signals to obtain all 16 components of the Mueller matrix. Two significant points of difference exist between the Azzam invention and the present invention. First, Azzam teaches the Fourier analysis of his scattering data. Since the Fourier series is truncated after the twelfth term according to Azzam's invention, the last few terms, for example, the eighth through twelfth terms, must be approaching zero rapidly in order for the truncation of the series to have meaning. Therefore, to extract several of the Mueller matrix elements, sums and differences of extremely small measurements having noise superimposed thereon must be taken. Since these numbers have decreasing signal-to-noise ratio, the matrix elements derived therefrom are unreliable. This is exactly the difficulty which exists for more direct measurements of linear combinations of the Mueller matrix elements. The present invention substantially avoids this difficulty. Moreover, Azzam restricts the modulation frequencies of the two required retarders to have a ratio of exactly five to one in order that simplifications occur in the Fourier transform mathematics. No such restriction is required for the successful practice of the subject invention.

W. E. Bickel and M. E. Stafford describe the measurement of scattered light from biological systems to yield optical data which can differentiate between species, strains, surface characteristics, etc. in "Polarized Light Scattering from Biological Systems: a Technique for Cell Differentiation," J. Biol. Phys. 9, 53 (1981). Therein the authors disclose that the 10 independent Mueller matrix elements or linear combinations thereof may be determined by combining scattering measurements involving the three possible polarization orientations of input radiation and the three polarization orientations of the scattered radiation plus a measurement of the total intensity. Polarization measurements of the type suggested therein require several different experimental arrangements involving different optical elements and are therefore tedious and time-consuming to achieve. The subject invention requires two configurations of a single experimental apparatus to accomplish the requisite measurements. Bickel and Stafford describe only one apparatus; one which uses a quarter-wave plate retarder for the analyzer optics, and which is therefore only capable of determining linear combinations of Mueller matrix elements with their inherent loss of significant information. That is, as detailed in a previous paper by Bickel entitled "Application of Polarization Effects in Light Scattering: A New Biophysical Tool," by W. S. Bickel, J. F. Davidson, D. R. Huffman, and R. Kilkson, Proc. Nat. Acad. Sci. U.S.A., Biophysics 73, 486 (1976), the coefficient $S_{34}^*$, which is a combination of $S_{14}$, $S_{34}$, $S_{11}$, and $S_{13}$, is the one obtained from the apparatus described in both references.

A useful summary of the theoretical background which is relevant to the subject invention may be found in "Measurement of Polarized Light Interactions via the Mueller Matrix," by Randall C. Thompson, Jerold R. Bottiger, and Edward S. Fry, Applied Optics 19, 1323 (1980), the disclosure of which is hereby incorporated by reference herein. Thompson et al. describe a four-modulator photopolarimeter capable of directly and simultaneously determining all sixteen Mueller matrix elements with a single apparatus utilizing light scattering measurements. Of particular importance in this reference is the implication that the use of smaller numbers of polarization modulators permits only the measurement of combinations of matrix elements. Thompson et al. therefore teach away from the present invention which uses two polarization modulators. It should be mentioned at this point that the use of four polarization modulators severely reduces the signal-to-noise ratio of the observed intensities over that for the two modulator configuration. Here the "signal" is the amplitude of the desired frequency component and "noise" is the amplitude of all undesired components. Also of importance in this reference is the choice of the retardance amplitude of 2.40483 radians which makes $J_o(\delta) = 0$. This removes the dc term from the expansion expressions for the Mueller matrix elements, and renders the dc component of $I_f$ proportional only to the 11 matrix elements. The use of only two polarization modulators in two configurations according to the teachings of the present invention to achieve a similar result to that obtained by Thompson et al. with the use of four modulators derives from the fortuitous circumstance that the higher order Bessel function terms appearing in the expressions for the Mueller matrix elements decrease sufficiently rapidly, to permit the desired unique modulation frequency dependence for each Mueller matrix element to be possible as is the case for Thompson et al.

SUMMARY OF THE INVENTION

Accordingly, it is an object of the present invention to provide an apparatus and method for rapidly characterizing biological particles, such as viruses, bacteria, and certain cells, to name a few biological particles, in static suspension.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus of this invention may include means for generating collimated, high intensity, substantially monochromatic radiation having a chosen wavelength, a first polarizer for polarizing the monochromatic radiation along a first axis, at most a single first modulator having a first retardance between ¼-wavelength and ½-wavelength of the substantially monochromatic radiation and having a first modulation frequency for generating elliptically polarized radiation from the linearly polarized radiation, means for holding the sample of biological particles and permitting the interaction between the particles under investigation and the elliptically polarized radiation to occur, at most a single second modulator having a second retardance of between ¼-wavelength and ½-wavelength of the substantially monochromatic radiation and a second modulation frequency for receiving a portion of the scattered radiation resulting from the interaction of the elliptically polarized incident radiation with the sample of biological particles, a second polarizer for receiving the scattered radiation bearing two modulation frequencies and polarizing this radiation along a second axis, means for quantitatively detecting the radiation passed by the second polarizer where the detecting means is sensitive to the frequencies present in the radiation passed by the second polarizer impressed thereon by the effect of the first and second modulators, and means for identifying and measuring the intensity associated with each individual frequency present in the radiation passed by the second polarizer, whereby the first and second axes and the first and second retardances are chosen such that the dc component of the intensity of the scattered radiation is independent of the polarization of the radiation so that a polarization independent normalization of the total scattered radiation can be achieved, and whereby the measured intensities at each of the frequencies present in the detected radiation have a substantially unique mathematical relationship to a particular Mueller matrix element deriving from the interaction of the incident radiation with both the optical elements of the apparatus and the biological particles under investigation such that eight independent matrix elements can be extracted from a single polarization configuration of the apparatus, which matrix elements when normalized by the intensity of the total scattered radiation contain information according to the identity of the biological particles under investigation. Preferably, the first and second polarization modulators include photoelastic modulators. It is also preferred that the first and second retardances are 2.40482 radians. A quarter-wave plate can be inserted between the means for holding the sample and the second polarization modulator if the $S_{23}$ and $S_{32}$ Mueller matrix elements are to be measured. The scattered radiation passes therethrough and interacts therewith to provide the additional information as will be described hereinbelow.

In a further aspect of the present invention, in accordance with its objects and purposes, the method hereof may include generating substantially monochromatic electromagnetic radiation having a chosen wavelength, linearly polarizing this radiation along a first axis, generating a first modulated elliptically polarized radiation therefrom which includes the superposition of waves having a phase lag between ¼- and ½-wavelength of the generated radiation and has a first modulation frequency, directing the first elliptically polarized radiation through the static suspension of biological particles to be analyzed permitting the interaction between the elliptically polarized radiation and the static suspension of biological particles to occur, thereby producing scattered radiation containing polarized information related to the biological particles, generating a second modulated elliptically polarized radiation from a portion of the scattered radiation emitted at a chosen scattering angle, this second elliptically polarized radiation including a superposition of waves having a phase lag between ¼- and ½-wavelength of the generated radiation and having a second modulation frequency, extracting a linearly polarized component of the second elliptically polarized radiation along a second axis, detecting the intensity of this component, the intensity bearing amplitude modulation at frequencies which are linear combinations of the first and second modulation frequencies, and extracting the magnitude of the intensity at certain of these frequencies, whereby eight independent Mueller matrix elements can be determined which contain information according to the nature of the suspension of biological particles. The measurements can be repeated at different scattering angles and interrogating radiation wavelengths to provide additional information about the biological particles. Preferably, a correction for the birefringence of any container holding the suspension of biological particles is made according to the description provided hereinbelow. In the actual identification procedure for an unknown biological particle, the measured Mueller matrix elements as a function of scattering angle and wavelength are compared with a database comprising many such measurements recorded for known samples.

Benefits and advantages of the present invention include the identification of low concentrations of biological particles in static fluid suspension on a timescale which is short compared with current analytical procedures, rendering this important investigation more useful.

BRIEF DESCRIPTION OF THE DRAWINGS

The accompanying drawings, which are incorporated in and form a part of the specification, illustrate one embodiment of the present invention and, together with the description, serve to explain the principles of the invention. In the drawings:

FIG. 3 shows the frequency dependence of the elements of the Mueller matrix for a particular choice of polarization modulator retardances and azimuthal angles for the passing axes of the polarizers and the fast axes of the polarization modulators.

DETAILED DESCRIPTION OF THE INVENTION

Figure 1:
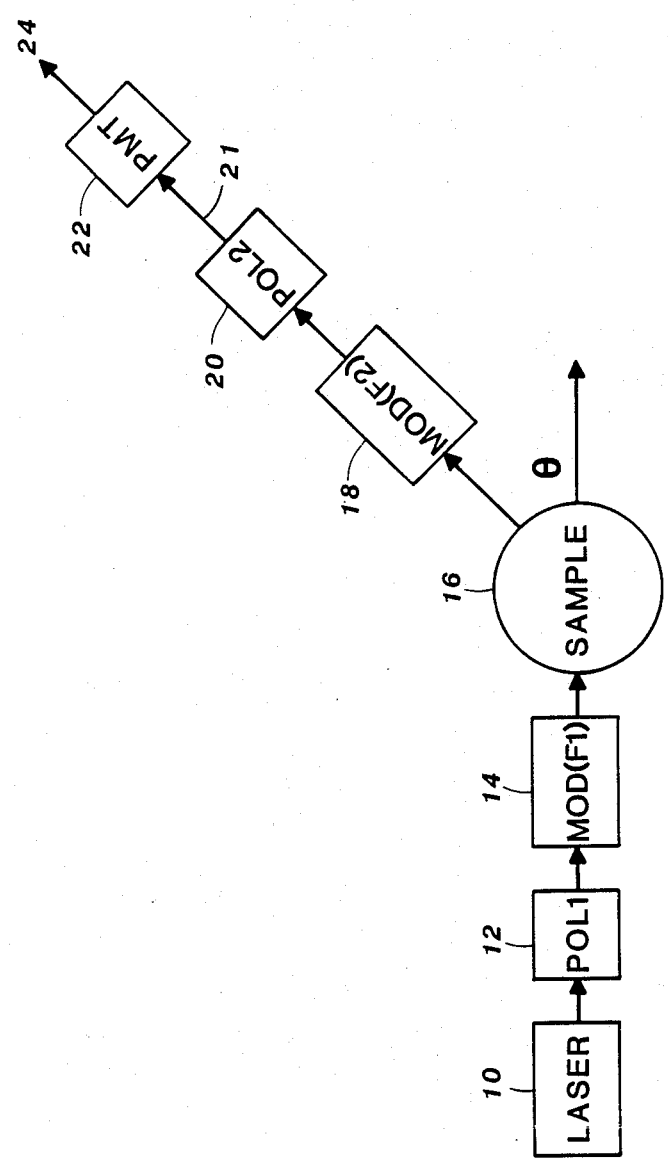
FIG. 1 shows a schematic representation of the apparatus of the present invention in its most elementary form.

The Mueller matrix is a 4×4 matrix which describes the polarization sensitive transformation of an incident beam of light into a scattered beam of light by a scattering object such as a biological particle or a suspension of biological particles. Much information concerning the internal structure and shape can be derived about the scattering particles from the simultaneous determination of multiple Mueller matrix elements at specific wavelengths and scattering angles, enough information in many cases to enable discrimination among a wide variety of different biological particles. Measurement of a sufficient number of polarization related phenomena to extract the ten independent Mueller matrix elements would be a formidable task involving many experimental configurations and difficult measurements. The present invention overcomes this difficulty by permitting all of the relevant information to be derived from the measurement of a single intensity using a single apparatus.

By defining the polarization of the radiation incident on the sample of biological particles to be elliptical polarization, choosing the retardances properly, and modulating this polarization before and after its interaction with the biological particles in the sample, one can achieve the encoding of the biological particle information contained in the Mueller matrix in the frequency dependence of the radiation intensity emerging from the sample and its attendant optical system. That is, the intensity can be manipulated to closely approximate the form $I(\theta,\lambda,f_{ij})=\Sigma_{ij}a(f_{ij})S_{ij}(\theta,\lambda)$, where $\theta$ and $\lambda$ are the scattering angle and the wavelength of the radiation, respectively, the $f_{ij}$ are the linear combinations of the two applied polarization modulation frequencies, $S_{ij}(\theta,\lambda)$ are the Mueller matrix elements, and $a(f_{ij})$ are combinations of trigonometric functions each having a unique frequency, $f_{ij}$, associated with it. It is an important element of the present invention that a series of measurements of the intensity at each of the frequencies, $f_{ij}$, permits the extraction of the individual Mueller matrix elements. That is, $S_{ij}(\theta,\lambda)=I(\theta,\lambda,f_{ij})/a(f_{ij})$, for each distinct combination $f_{ij}$. Lock-in amplifiers are used to detect the typically small signals at each frequency. Requirements for the intensity of the interrogating radiation are quite modest since the measurements are performed in small cuvettes containing the biological particle suspension, with no particular time constraints for the measurement. Biological particle samples were prepared substantially as follows:

1. Bacteria.

Bacterial suspensions were streaked on a suitable nutrient agar and placed in an incubator overnight. Several individual colonies were later removed from the plate and suspended in phosphate buffered saline. The concentrated suspensions were diluted to a concentration that did not give multiple particle scattering, but did give an acceptable MLS spectrum. Aliquots of the final concentration used were then occasionally diluted and spread on nutrient agar for colony counting. The usual bacterial concentration that gave useful spectra was approximately $10^5$ organisms (colony forming units)/cc.

2. Virus.

The viral preparations used were derived from vaccines containing inactivated virus, viral fragments, cell debris, and soluble protein from either egg allantoic fluid or mouse brain extracts. The egg preparations contained particulate material (probably urate crystals) that was removed by filtration through cheesecloth before use. The crude suspensions were then diluted in phosphate buffered saline for use as described hereinabove. The concentration required for useful scattering spectra was approximately $10^7$ viral particles/cc, but the precise concentration could not be measured. A sample specimen was thereby prepared having a small remaining liquid volume containing essentially a single species of biological particle in suspension. Clinical specimens would be processed in a similar manner. The sample is then placed in a cuvette and placed in the path of the interrogating beam which has been suitably prepared as to its polarization. A reference frequency generator is sequentially switched by a computer to the first of eight reference frequencies, each frequency corresponding to a particular Mueller matrix element, and a scattered light intensity measurement made by using a lock-in amplifier tuned to each reference frequency in turn. Measurements were made with a 1 to 3 second time constant, but longer or shorter integration times are possible if the particle concentration is low. The signal corresponding to each selected Mueller matrix element is digitized and compared with Mueller matrix elements previously stored in a database in order to determine the identity of the sample of suspended biological particles under investigation. It is of course straightforward to determine whether a virus, bacteria or other cell database is to be used to identify the biological particles in the specimen suspension. By performing the measurements in this manner, difficult polarization measurements are avoided, and the individual matrix elements emerge without the need for solving systems of equations with diminutive terms. As mentioned hereinabove, Thompson et al. achieve a similar result, but require the use of four polarization modulation frequencies. According to the present invention, eight Mueller matrix elements can be determined for each of two choices of the azimuthal angles for the polarizer passing axes and polarization modulator fast axes. Adjustment of the present apparatus from one set of chosen azimuthal angles to the other does not require any substitution of components but only simple adjustments to the components in place. As will be described hereinbelow, the measurement of the $S_{32}$ and $S_{23}$ matrix elements require the insertion of a quarter-wave plate between the sample and the second polarization modulator.

It should be mentioned that the present invention can be used only for the identification of biological particles for which a substantially homogeneous suspension can be prepared. Bacteria in a clinical specimen often represent a very heterogeneous population since many strains of bacteria frequently coexist. Therefore, procedures for separating the specimen into its component parts must be employed as briefly described hereinabove. Although clinical virus specimens generally involve a single virus species, the virus particles must be separated from bacteria and other biological particles accompanying the virus in the sample. In order to avoid detailed separation of biological particles, a flow cytometer in which the particles are analyzed one-at-a-time as they pass through the focused incident light beam is required. The DNA in a bacterium is organized in supercoils which are randomly oriented in space. As a result, a detector in the flow cytometer apparatus would observe the same differential scattering signal regardless of the orientation of the bacterium. Viruses, as oriented particles, cannot as readily be analyzed in such a manner because of the much more complicated scattering signals generated thereby. Such an apparatus is described in U.S. Pat. application Ser. No. 06/815,185, "Optically Active Biological Particle Distinguishing Apparatus," filed on Dec. 13, 1985 by G. C. Salzman et al.

Turning now to the drawings, FIG. 1 is a schematic representation of the apparatus of the present invention in its most basic form. Substantially monochromatic light from a light source such as a laser 10 (argon ion laser operating at between 50 and 250 mW output power) is directed into a first polarizer 12 to insure that a substantial fraction of the transmitted radiation is linearly polarized at a specific angle with respect to the horizontal scattering plane. The emerging beam is then directed to a photoelastic modulator 14 operating at 50 kHz wherein the radiation is elliptically polarized with its handedness alternating left and right at 50 kHz. The radiation emerging from the polarization modulator is then made incident on the sample 16 held in a cylindrical quartz cuvette 50 mm in diameter with 2 mm thick walls. The incident intensity is not modulated by these optical elements. Transmitted radiation is directed into a Rayleigh horn (not shown) to minimize stray scattered light.

The scattered light analyzing and detecting components of the present apparatus are mounted on a computer-controlled rotary stage. The scattering angle, $\theta$, in the horizontal plane is defined relative to the incident radiation, and the acceptance half-angle for the analyzing and detecting components was about 0.5°. Scattered radiation to be observed at a particular scattering angle is passed through a second photoelastic modulator 18 which was operated at 47 kHz, and then directed into a second linear polarizer 20. The emerging light 21 is passed through a wavelength filter (not shown) to remove satellite laser wavelengths and made to impinge on a detector 22 sensitive to the wavelength employed. As will be described in Example II hereinbelow, if direct measurements of the $S_{23}$ or $S_{32}$ Mueller matrix elements are desired, a quarter-wave plate (not shown) may be inserted between the sample cuvette and the second photoelastic modulator 18. The retardances of the two modulators 14, 18 were selected to be 2.4048 radians in order to render the total scattered intensity, which is used to normalize the other Mueller matrix elements, independent of the polarization of the scattered light. With the use of two modulators, eight of the Mueller matrix elements can be measured simultaneously; this number being all of the independent matrix elements measurable by any scattering experiments since the remaining matrix elements are derivable therefrom. The two modulation frequencies produce intensity modulation at the photomultiplier tube at several frequencies which are linear combinations of the two input frequencies.

Figure 2:
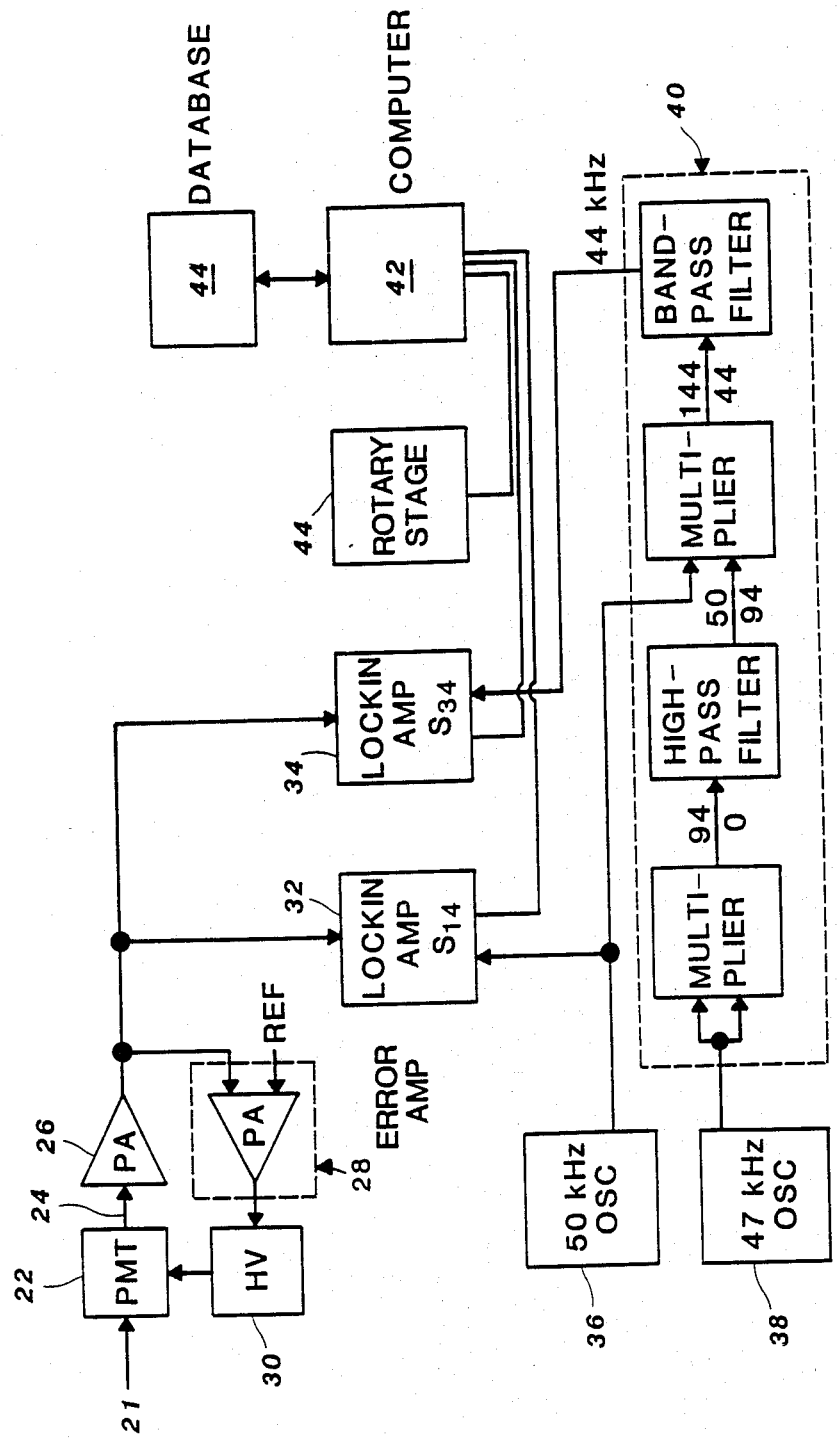
FIG. 2 shows a schematic representation of the detection and measurement portion of the apparatus of the present invention in the configuration used to determine the $S_{14}$ and $S_{34}$ Mueller matrix elements.

FIG. 2 shows a block diagram of the electronic circuitry used for measuring $S_{14}$ and $S_{34}$ Mueller matrix elements. Photomultiplier tube 22 is powered by a high voltage power supply 30. Preamplifier 26 both increases the amplitude of the signal 24 from the photomultiplier in order to drive the lock-in amplifiers 32, 34, and is part of a feedback loop 26, 28, 30 for maintaining the anode current of the photomultiplier constant by controlling the high voltage bias on the photomultiplier tube as the scattering angle is changed. This effectively normalizes all of the matrix elements to the total scattered intensity. Computer 42 drives a rotary stage 44 which changes the scattering angle observed by the analyzing optics, receives the signals generated by the lock-in amplifiers (only two signals in the situation described), and compares the normalized results with those stored in database 44 in order to identify the biological particle in the suspension. An oscillator 36 operating at 50 kHz provides the reference frequency for one lock-in amplifier 32, while a second oscillator 38 operating at 47 kHz drives a frequency multiplier/filter chain 40 which provides a 44 kHz reference frequency to the second phase lock-in amplifier. The choice of this reference frequency will become apparent in the discussion which follows. It should be mentioned at this point that the number of lock-in amplifiers employed is a function of the number of desired independent Mueller matrix elements. That is, since each Mueller matrix element occurs at a distinct frequency and each lock-in amplifier is electrically referenced to a single frequency, the simultaneous measurement of eight Mueller matrix elements for a chosen set of polarizer passing axes and polarization modulator fast axes will require eight phase-sensitive detectors. Determination of the Mueller matrix elements as a function of wavelength and scattering angle for many suspension of biological particles will provide a database from which unknown suspensions will be able to be compared in order to quickly identify the unknown sample.

Having generally described the invention, the following specific examples are given as a further illustration thereof.

EXAMPLE I

If the azimuthal angle, $\gamma$, is defined as being positive in a clockwise manner measured from the horizontal scattering plane in which the scattering angle $\theta$ is defined and looking into the beam of radiation incident on the sample under investigation, and the azimuthal angle of the passing axis of each of the polarizers is $+45°$ while that for the fast axis for each of the polarization modulators is $+90°$, the measurable matrix elements of the Mueller matrix are shown in FIG. 3. The numbers in parentheses are the frequencies in kilohertz at which each matrix element is determined. The dashes in some of the parentheses indicate that there is no contribution from that particular matrix element. With the polarizer passing axes set at $+90°$, and the modulator fast axes set at $+45°$, however, row 3 and column 3 are missing. $S_{11}$ is the total scattering intensity and appears as a dc component at zero frequency. $S_{14}$ is the circular intensity differential scattering term, $I_L - I_R$, $I_L + R$ and appears at 50 kHz. The other polarization sensitive element of particular interest is $S_{34}$ which appears at 44 kHz. With row 3 and column 3 missing instead of row 2 and column 2, $S_{24}$ appears at 44 kHz instead of $S_{34}$. The results for several virus vaccines are shown in FIGS. 4 and 5.

Figure 4:
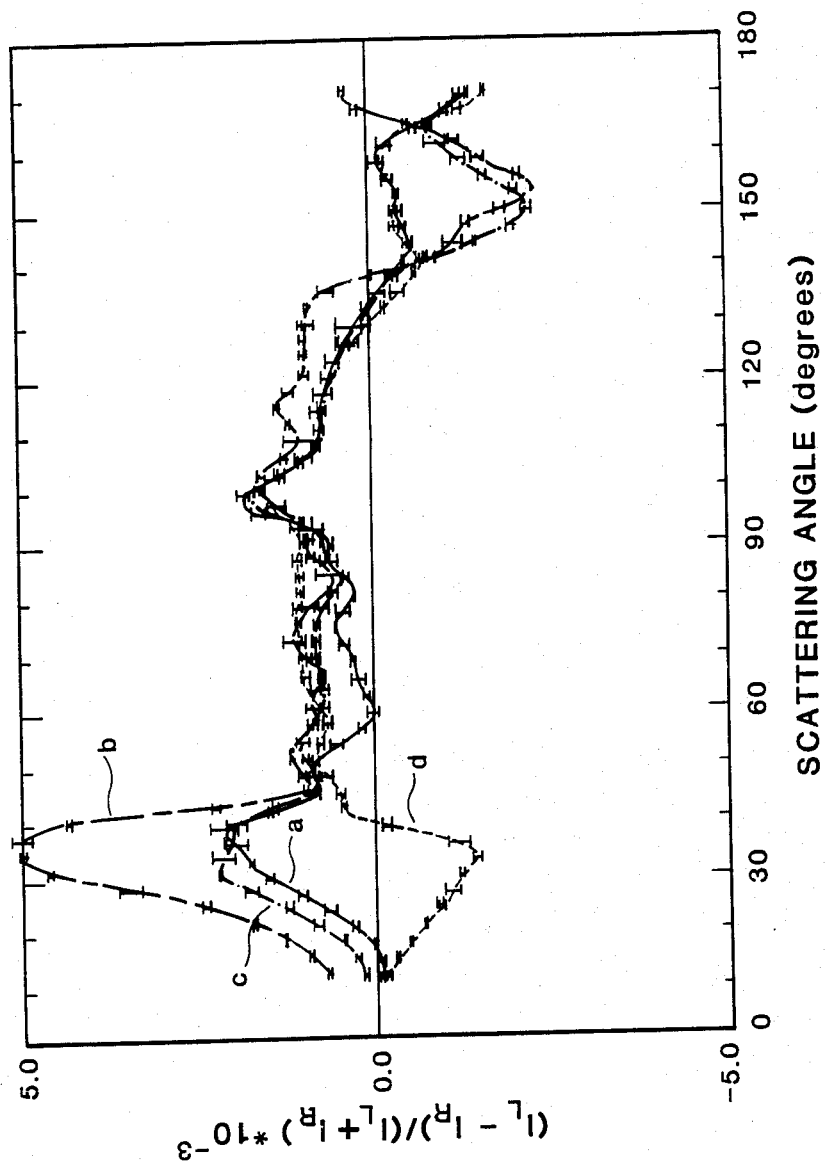
FIG. 4 is a graph of $S_{14}$ as a function of scattering angle at 360 nm for four classes of encephalitis virus vaccines.
Figure 5:
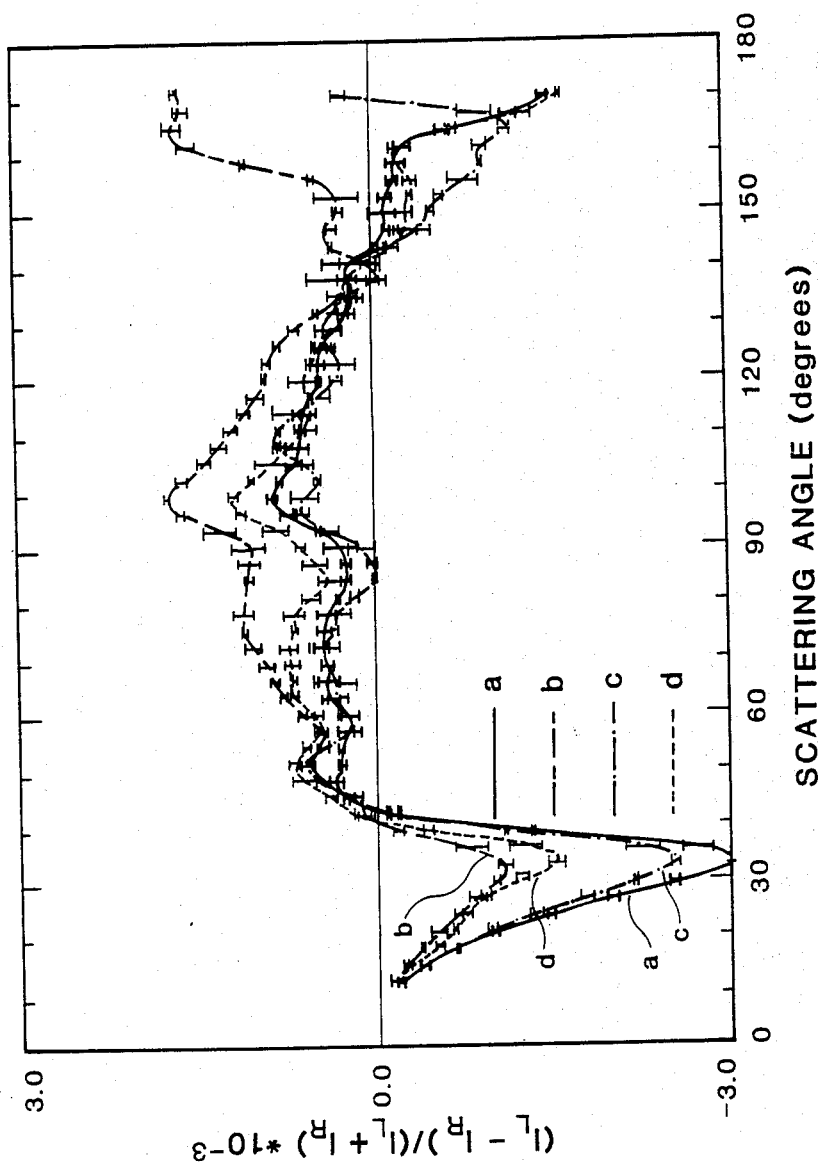
FIG. 5 is a graph of $S_{14}$ as a function of scattering angle at 360 nm for four classes of dengue fever virus vaccines.

FIG. 4 shows plots of $S_{14}$ for four types of encephalitis virus vaccines as a function of scattering angle at 360 nm. The plot for VEE, Venezuelan Equine Encephalitis (TC-83) is denoted by "a", "b" is the plot for SLE, St. Louis Encephalitis (TBH-28), "c" is the plot for WEE, Western Equine Encephalitis (Fleming) and "d" is the plot for EEE, Eastern Equine Encephalitis plots of $S_{14}$ for four types of dengue fever virus vaccines as a function of scattering angle at 360 nm. As in FIG. 4, the four viral types are readily distinguishable at 30° scattering angle within the experimental variation indicated by the error bars. The plot for Dengue Type 1 (Hawaii) is denoted by "a", "b" is the plot for Dengue Type 2 (New Guinea), "c" is the plot for Dengue Type 3 (H879), and "d" is the plot for Dengue Type 4 (H24L). The St. Louis Encephalitis Virus is difficult to distinguish from Dengue Fever Virus serologically. The circular intensity differential scattering spectra for the vaccine preparations are, however, very different. Clearly, to obtain additional information about each virus, especially those which have similar scattering angle or wavelength plots for particular matrix element, other Mueller matrix elements would be measured.

Each of the Mueller matrix elements is calibrated by rotating the detector to 0° scattering angle and replacing the sample cuvette with various combinations of optical elements whose Mueller matrices are known. For example, $S_{14}$ and $S_{34}$ are calibrated by inserting a 488 nm quarter-wave plate with its fast axis at 0° followed by a polarizer. The polarizer is rotated in steps through azimuthal angles ranging from 0° to 180°. $S_{14}$ behaves as the sine of twice the azimuthal angle and $S_{34}$ behaves as the sine squared of twice the azimuthal angle. The lock-in amplifier gain corrections for $S_{14}$ and $S_{34}$ can thereby be determined and stored in the computer for use in obtaining a set of Mueller matrix elements which is representative of a particular virus. A similar procedure is followed for the remaining matrix elements. These calibrations also enable the determination of the correct phase offsets between the reference and signal waveforms.

EXAMPLE II

Example I describes the extraction of fourteen out of the sixteen Mueller matrix elements in two measurements of eight matrix elements each, ten of which are independent. The additional matrix elements might be useful for investigating the measurement precision but could be obtained by appropriate combinations of the measured elements. In this regard, the $S_{23}$ and $S_{32}$ matrix elements, which cannot be obtained in the manner described hereinabove, are extracted according to the following procedure if these elements are desired:

With the azimuthal angle, $\gamma$, of the passing axis for each of the first and second polarizers set at 90°, the fast axis of each of the first and second polarization modulator set at 45°, the elements 21, 41, 12, 22, 42, 14, 24 and 44 are determined, as described in Example I and will hereinafter be designated as I configuration. Moreover, if the azimuthal angle for the passing axis for each of the polarizers is 45°, and that for the fast axis for each of the polarization modulators is 90°, the matrix elements 31, 41, 13, 33, 43, 14, 34, 44 are determined, which will hereinafter be designated as configuration II. If a quarter-wave plate having its fast axis oriented at 0° azimuthal angle is inserted between the sample cuvette and the second polarization modulator, and if the remaining azimuthal angles are arranged according to configuration I, matrix elements 21, 31, 12, 22, 32, 14, 24, and 34, can be determined. Similarly, if the azimuthal angle of the fast axis of the quarter-wave plate is set at 45° while the remaining azimuthal angles are arranged according to configuration II, matrix elements 21, 31, 13, 23, 33, 14, 24, and 34 can be determined. It should be mentioned at this point that $S_{11}$, the polarization independent scattered intensity related matrix element is always determined if anything at all is to be measured.

Ideally, the cuvette should exhibit no strain birefringence at either the light input or output locations. A strain of less than 10 nm of retardance at a specified wavelength per centimeter of cuvette light transmitting material is considered strain free in the optics industry. $S_{14}$ is affected only by strain at the input location, while $S_{34}$ is affected equally by strain at both the input and output locations. Strain at the input location causes $S_{12}$ and $S_{13}$ to have contributions at the same frequency as that for $S_{14}$. Since $S_{12}$ can be as large as $-1$ (at 90° scattering angle), this represents a potentially severe problem for extracting independent Mueller matrix elements. Modeling studies indicate, however, that for cuvette input light transmitting material strains as large as 24.4 nm/cm, an $S_{12}$ value of $-0.5$, and an $S_{14}$ value of 0.001, the contribution at 50 kHz from $S_{14}$ is twice as large as that from $S_{12}$, and the $S_{12}$ contribution does not change as the $S_{14}$ value varies over a wide range. This calculation was performed for the situation where the azimuthal angle for the passing axis of each of the polarizers was $+45°$, that for the fast axis for each of the polarization modulators was $+90°$, and the fast axis for the strain was $+45°$ with respect to the horizontal scattering plane. The modeling calculations also indicate that if a set of measurements is performed for both choices of azimuthal angle described hereinabove, the degree of strain and the orientation of its fast axis at each of the input and output locations will be able to be determined. Once these four numbers are determined, each Mueller matrix element can be appropriately corrected. That is, the two chosen azimuthal angle configurations can give rise to fourteen pieces of information: ten independent Mueller matrix elements, and the four required degree of strain parameters.

EXAMPLE III

Figure 6:
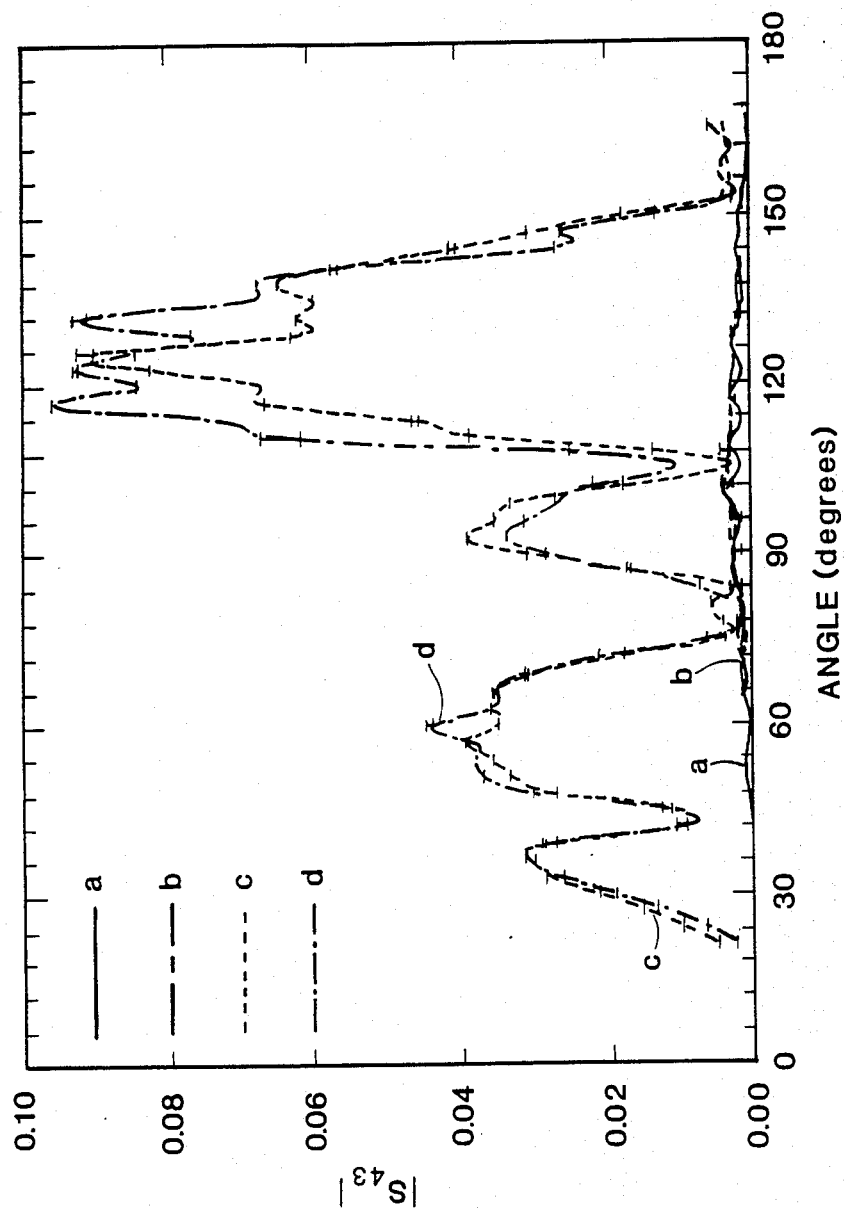
FIG. 6 is a graph of $|S_{43}|$ as a function of scattering angle at 488 nm for four types of bacteria.
Figure 7:
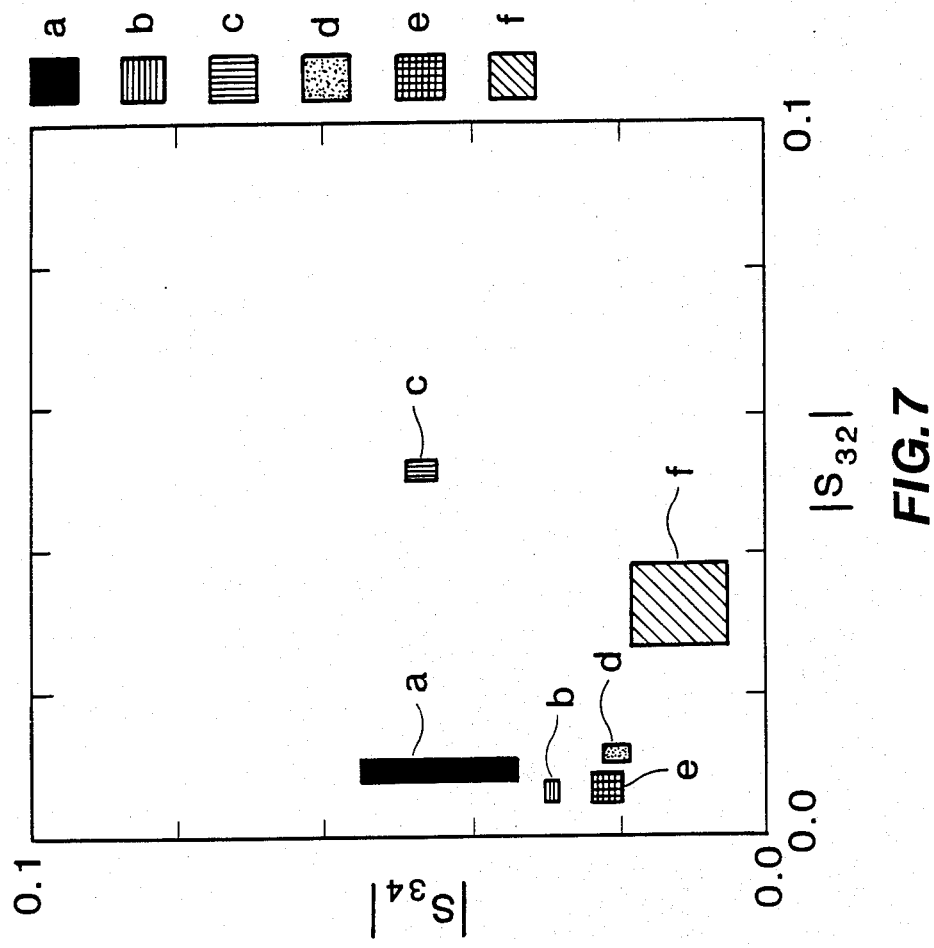
FIG. 7 shows a plot of $S_{34}$ versus $S_{32}$ for six types of bacteria at 488 nm and at 60° scattering angle.

Whereas FIGS. 4 and 5 concern data collected for several viruses, FIGS. 6 and 7 show corresponding data for bacteria. Turning now to FIG. 6 hereof, a graph of the absolute value of $S_{43}$, $|S_{43}|$ versus scattering angle for four bacteria strains is shown. Curves a–d represent *Klebsiella pneumoniae* (KPNEU001), *Klebsiella pneumoniae* (KPNEU002), *E coli* B (ECOLB104), and *E coli* B (ECOLB105), respectively. Approximately $10^5$ particles/cc of each strain gave the results shown. FIG. 6 shows a graph of $S_{34}$ versus $S_{32}$ for six strains of bacteria at 488 nm and a scattering angle of 60°. Boxes a–f represent *E coli* B, *E coli* K12, *Klebsiella pneumoniae*, *Proteus mirabilis*, *Flavobacterium meningosepticum* and *Vibrio fluvialis*, respectively. It is apparent that it would be straightforward indeed to distinguish *Klebsiella pneumoniae* from *Vibrio fluvialis*, for example, while the differences among *E coli* B and *E coli* K12 are not as substantial. Other Mueller matrix elements may provide significant distinction among the various strains of bacteria. It is to be observed that usable data may be obtained from $10^5$ bacteria particles per cubic centimeter of suspension, whereas $10^7$ virus particles per cubic centimeter of suspension are required to yield similar quality data.

The foregoing description of the preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What we claim is:

1. An apparatus for the identification of biological particles in static fluid suspension which comprises in combination:
   a. means for generating collimated, high intensity, substantially monochromatic radiation having a chosen wavelength;
   b. a first polarizer for receiving and substantially linearly polarizing the substantially monochromatic radiation, the resulting polarized radiation being emitted from said first polarizer having a polarization directed along a first axis;
   c. at most a single first modulator having a first retardance of between $\frac{1}{4}$-wavelength and $\frac{1}{2}$-wavelength of said emitted polarized radiation for receiving said linearly polarized radiation and for generating polarization modulated elliptically polarized radiation therefrom, the modulation having a first frequency;
   d. means for receiving the particle sample to be identified, for permitting the modulated elliptically polarized radiation to enter and interact with the biological particles, and for permitting the radiation scattered thereby to emerge;
   e. at most a single second modulator having a second retardance of between $\frac{1}{4}$-wavelength and $\frac{1}{2}$-wavelength of the emitted polarized radiation for receiving a portion of the emerging scattered radiation at a chosen angle and for generating polarization modulated radiation therefrom having a second modulation frequency simultaneously impressed thereon;
   f. a second polarizer for receiving the scattered radiation bearing two polarization modulation frequencies and interacting therewith to pass a component of the scattered radiation having its polarization directed along a second axis, the first retardance and the second retardance, and the first axis and the second axis being chosen such that the dc component of the intensity of the scattered radiation is independent of polarization in order that a normalization of the scattered radiation can be achieved;
   g. means for quantitatively detecting the radiation passed by said second polarizer, said quantitative detection means having sensitivity to each individual frequency of a plurality of frequencies present in the radiation passed by said second polarizer, the individual frequencies resulting from the effect of said first polarization modulator and said second polarization modulator on the emitted polarized radiation and the scattered radiation, respectively; and
   h. means for identifying and measuring the intensity associated with each individual frequency of the plurality of frequencies present in the quantitatively detected radiation passed by said second polarizer, each of the intensities thereby identified and measured having a definite mathematical relationship substantially to a particular Mueller matrix element, the Mueller matrix elements deriving from the interaction of the biological particles with the polarization modulated elliptically polarized radiation; whereby eight matrix elements can be extracted, the matrix elements, when normalized by the intensity of the scattered radiation, containing information according to the nature of the biological particles under investigation.

2. The apparatus as described in claim 1, wherein a quarter-wave plate is inserted between said means for receiving the biological particle sample to be identified and said second modulator, whereby the emerging scattered radiation passes therethrough and interacts therewith before entering said second modulator, thereby permitting the measurement of the $S_{23}$ and $S_{32}$ Mueller matrix elements to be made.

3. The apparatus as described in claims 1 or 2, wherein said first modulator and said second modulator include photoelastic modulators, said photoelastic modulators having sinusoidally varying retardance amplitudes at the first frequency and the second frequency, respectively.

4. The apparatus as described in claim 3, wherein the first retardance and the second retardance are each chosen to be 2.40483 radians.

5. The apparatus as described in claim 4, wherein said means for identifying and measuring the intensity associated with each individual frequency of the plurality of frequencies includes at least one phase-sensitive detector, said at least one phase-sensitive detector being tunable in turn to each individual frequency and being capable of measuring the intensity of the quantitatively detected radiation appearing at said at least one phase-sensitive detector and derived from said quantitatively detecting means, thereby permitting the evaluation of the Mueller matrix elements.

6. An apparatus for the identification of biological particles in static fluid suspension which comprises in combination:
   a. a laser for producing collimated, high intensity, substantially monochromatic radiation having a chosen wavelength and having substantial polarization along a first axis;
   b. at most a single first modulator having a first retardance of between $\frac{1}{4}$-wavelength and $\frac{1}{2}$-wavelength of the substantially monochromatic laser radiation for receiving the linearly polarized radiation and for generating polarization modulated elliptically polarized radiation therefrom, the modulation having a first frequency;
   c. means for receiving the biological particle sample to be identified, for permitting the modulated elliptically polarized radiation to enter and interact with the biological particles, and for permitting the radiation scattered thereby to emerge;
   d. at most a single second modulator having a second retardance of between $\frac{1}{4}$-wavelength and $\frac{1}{2}$-wavelength of the emitted polarized radiation for receiving a portion of the emerging scattered radiation at a chosen angle and for generating polarization modulated radiation therefrom having a second modulation frequency simultaneously impressed thereon;
   e. a first polarizer for receiving the scattered radiation bearing two polarization modulation frequencies and interacting therewith to pass a component of the scattered radiation having its polarization directed along a second axis, the first retardance and the second retardance, and the first axis and the second axis being chosen such that the dc component of the intensity of the scattered radiation is independent of polarization in order that a normalization of the scattered radiation can be achieved;

f. means for quantitatively detecting the radiation passed by said first polarizer, said detection means having sensitivity to each individual frequency of a plurality of frequencies present in the radiation passed by said first polarizer, the individual frequencies resulting from the effect of said first polarization modulator and said second polarization modulator on the emitted polarized radiation and the scattered radiation, respectively; and g. means for identifying and measuring the intensity associated with each individual frequency of the plurality of frequencies present in the quantitatively detected radiation passed by said first polarizer, each intensity thereby identified and measured having a definite mathematical relationship substantially to a particular Mueller matrix element, the Mueller matrix elements deriving from the interaction of the biological particles with the polarization modulated elliptically polarized radiation, whereby eight matrix elements can be extracted, the matrix elements, when normalized by the intensity of the scattered radiation, containing information according to the nature of the biological particles under investigation.

7. The apparatus as described in claim 6, wherein a quarter-wave plate is inserted between said means for receiving the biological particle sample to be identified and said second modulator, whereby the emerging scattered radiation passes therethrough and interacts therewith before entering said second modulator, thereby permitting the measurement of the $S_{23}$ and $S_{32}$ Mueller matrix elements to be made.

8. The apparatus as described in claims 6 or 7, wherein a first polarizer is inserted between said laser and said first modulator for receiving and polarizing the substantially monochromatic laser radiation, the polarized radiation being emitted from said second polarizer having a polarization directed along a third axis; whereby the first retardance and the second retardance, and the second axis and the third axis are chosen such that the dc component of the intensity of the scattered radiation is independent of polarization in order that a normalization of the scattered radiation is independent of polarization so that a normalization of said scattered radiation can be achieved.

9. The apparatus as described in claim 8, wherein said first modulator and said second modulator include photoelastic modulators, said photoelastic modulators having sinusoidally varying retardance amplitudes at the first frequency and the second frequency, respectively.

10. The apparatus as described in claim 9, wherein the first retardance and the second retardance are each chosen to be 2.40483 radians.

11. The apparatus as described in claim 10, wherein said means for identifying and measuring the intensity associated with each individual frequency of the plurality of frequencies includes at least one phase-sensitive detector, said at least one phase-sensitive detector being tunable in turn to each individual frequency and being capable of measuring the intensity of the quantitatively detected radiation appearing at said at least one phase-sensitive detector and derived from said quantitatively detecting means, thereby permitting the evaluation of the Mueller matrix elements.

12. A method for the characterization and identification of samples of biological particles in static suspension, said method comprising the steps of:

a. generating substantially monochromatic electromagnetic radiation having a chosen wavelength;

b. linearly polarizing the resulting generated monochromatic radiation along a first axis;

c. generating at most a single first modulated elliptically polarized radiation from the polarized monochromatic radiation, the first modulated elliptically polarized radiation being a superposition of waves having a phase lag of between ¼-wavelength and ½-wavelength of the substantially monochromatic radiation, and having a first modulation frequency;

d. directing the first modulated elliptically polarized radiation through the biological particle suspension to be analyzed;

e. allowing the first modulated elliptically polarized radiation to interact with the biological particles, thereby producing scattered radiation containing polarization information related to the suspended particles;

f. generating at most a single second modulated elliptically polarized radiation from a portion of the scattered radiation emitted from the static suspension of biological particles at a chosen scattering angle, the second modulated elliptically polarized radiation being a superposition of waves having a phase lag of between ¼-wavelength and ½-wavelength of the substantially monochromatic radiation, and having a second modulation frequency;

g. extracting a linearly polarized component from the second modulated elliptically polarized radiation along a second axis;

h. detecting the intensity of the linearly polarized component along the second axis, the intensity bearing amplitude modulation at certain frequencies which are linear combinations of the first modulation frequency and the second modulation frequency; and i. extracting the magnitude of the intensity at certain frequencies; whereby eight Mueller matrix elements are measured substantially independent of each other, the Mueller matrix elements bearing information according to the nature of the suspension of biological particles under investigation.

13. The method as described in claim 12, wherein said steps a. to i. are repeated at a plurality of scattering angles.

14. The method as described in claims 12 or 13, wherein said steps a. to i. are repeated for a plurality of wavelengths.

15. The method as described in claim 14, further comprising the step of correcting for substantial strain birefringence resulting from the performance of said step of allowing the first modulated elliptically polarized radiation to interact with the biological particles producing the scattered radiation.

16. The method as described in claim 15, further comprising the step of comparing the measured Mueller matrix elements for the suspension of biological particles under investigation to a database of measured Mueller matrix elements for known static suspensions of biological particles, thereby permitting the identification of the biological particles under investigation to be achieved.

* * * * *